United States Patent [19]
Corio

[11] 3,934,584
[45] Jan. 27, 1976

[54] BALLING GUN

[76] Inventor: Nicholas N. Corio, 6932 W. Pershing Ave., Peoria, Ariz. 85345

[22] Filed: Sept. 26, 1973

[21] Appl. No.: 401,037

[52] U.S. Cl. ............................... 128/223; 128/264
[51] Int. Cl.² .................... A61D 7/00; A61M 31/00
[58] Field of Search ........... 128/223, 222, 264, 217, 128/261, 263, 237, 238, 127, 130; 221/232, 268, 279; 222/256

[56] References Cited
UNITED STATES PATENTS

| | | | |
|---|---|---|---|
| 2,269,963 | 1/1942 | Wappler | 221/279 X |
| 2,587,364 | 2/1952 | Mitchell | 128/264 |
| 2,601,852 | 7/1952 | Wendt | 128/264 |
| 2,754,822 | 7/1956 | Emelock | 128/264 |
| 3,595,233 | 7/1971 | Fuchslocher et al. | 128/264 |
| 3,757,781 | 9/1973 | Smart | 128/223 |

FOREIGN PATENTS OR APPLICATIONS

| | | | |
|---|---|---|---|
| 522,404 | 3/1931 | Germany | 128/217 |
| 1,478,493 | 3/1967 | France | 128/264 |
| 1,107,782 | 8/1955 | France | 128/223 |

Primary Examiner—Richard A. Gaudet
Assistant Examiner—Rick Opitz
Attorney, Agent, or Firm—Cahill, Sutton & Thomas

[57] ABSTRACT

A thumb operated balling gun for discharging a bolus within the throat of an aminal is disclosed. A plunger, responsive to the movement of an operator's thumb, is axially slidable within a barrel having a plurality of resilient arms extending therefrom. The resilient arms, in combination with the barrel, are particularly configured to avoid damaging the delicate tissues within the mouth and the throat of the animal. A collar, circumscribing the plunger and contacting the interior surface of the resilient arms on retraction of the plunger forces the resilient arms to open and permit insertion of a bolus within the grasp of the arms. After insertion of the bolus, slight extension of the plunger disassociates the collar from the arms, whereby the latter close upon the bolus and retain it in place. Further extension of the plunger ejects the bolus from within the grasp of the arms and into the throat of the animal.

10 Claims, 4 Drawing Figures

BALLING GUN

The present invention relates to medicinal dispensing apparatus, and, more particularly, to balling guns.

Balling guns have been and are presently extensively used by veterinarians, farmers, and others for administering medicinal cartridges of one form or another to livestock and other domestic animals. The medicinal cartridges may contain vitamins or curative medicines or a combination thereof. To provide for a range of cartridge size without requiring several different sized balling guns, an expandable mechanism has been incorporated at the extremity of the balling gun. In example, U.S. Ser. No. 453,508, teaches the use of a pair of oppositely disposed spring arms for engaging a bolus. Normally, the animal will struggle to some extent when the balling gun is inserted into the animal's mouth and throat. During such a struggle, it is not unusual for the bolus to become disengaged from in between the spring arms as the latter only exert a retaining force in one lateral direction.

To minimize the loss of the cartridge during insertion into the animal's throat, balling guns were developed to include an open ended cylinder mounted at the extremity of a long handle and adapted to receive the cartridges, or boluses. The handle was used to position the cylinder within the throat of the animal. Means were also included for ejecting the bolus from within the cylinder into the animal's throat. As the cylinders were configured to receive a bolus of a specified size, larger or smaller boluses could not be conveyed by the cylinder, or might have inadvertently fallen out of the cylinder during the insertion of the cylinder into the animal's throat. For these reasons, it was generally necessary to purchase the boluses from a specified manufacturer who made the boluses in a specific size to fit the cylinder of the balling gun. In the alternative, the cylinder was made detachable whereby a plurality of different sized cylinders could be attached to accommodate different sized boluses. Examples of such devices are shown in U.S. Pat. Nos. 1,325,699, 1,868,308, 2,170,599, 2,601,852, 2,621,655, 2,650,593 and 3,238,941.

In an effort to incorporate the beneficial features of resilient arms, which are adaptable to various sized medicinal cartridges or boluses, and cylinders, which cylinders reasonably firmly protected the cartridge against dislodgement, a balling gun incorporating both features was developed, as shown in United States Pat. No. 2,587,364. This device, while satisfactorily retaining and ejecting the bolus, required that the bolus retaining mechanism be of substantially greater cross-sectional area than that of the bolus.

It is therefore a primary object of the present invention to provide a balling gun useable with variously sized boluses.

Another object of the present invention is to provide a balling gun of minimum cross-sectional area.

Yet another object of the present invention is to provide a balling gun which will prevent lateral displacement of a bolus during insertion of the bolus into an animal's throat.

A further object of the present invention is to provide a balling gun which may be operated with one hand.

A still further object of the present invention is to provide a balling gun with automatically opening resilient arms to receive a bolus.

A still further object of the present invention is to provide a balling gun having contracted resilient arms during withdrawal of the balling gun from the animal's throat.

These and other objects of the present invention will become apparent to those skilled in the art as the description thereof proceeds.

The present invention may be described with greater specificity and clarity with reference to the following figures, in which.

Figure 3:
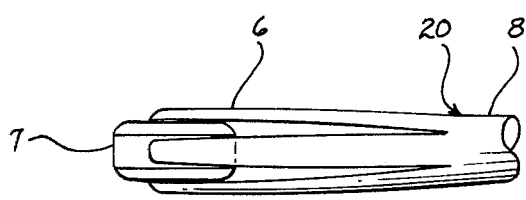

FIG. 3 particularly illustrates the configuration of the resilient arms to afford compact closure of the arms after the bolus is ejected.

Figure 2:
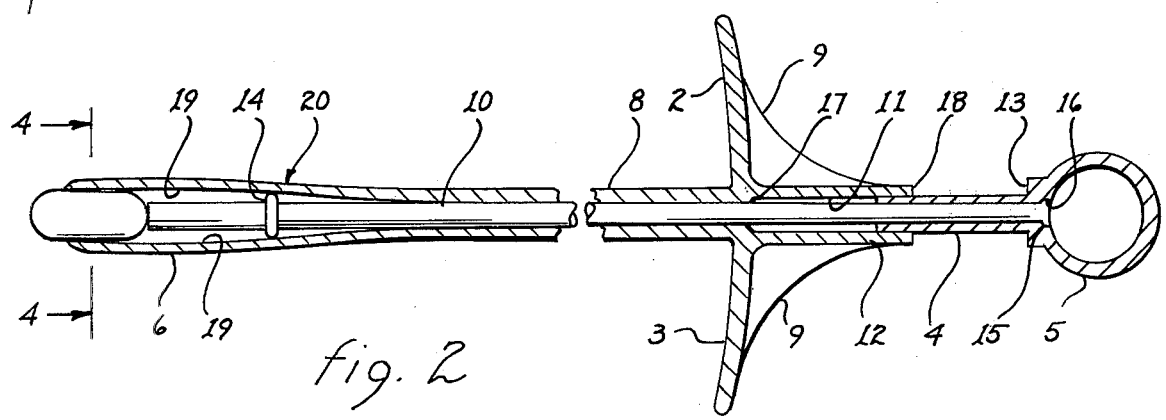
FIG. 2 illustrates a cross-sectional view of the components of the present invention.
Figure 4:
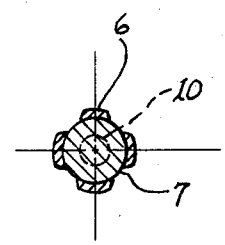

FIG. 4 illustrates a cross-sectional view of the present invention taken along lines 4—4, as shown in FIG. 2.

Figure 1:
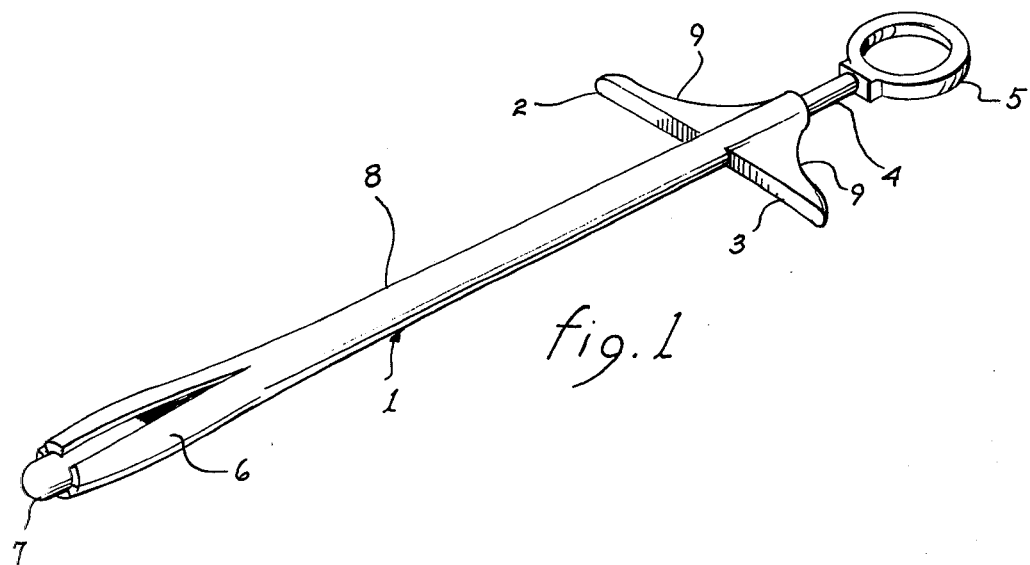
FIG. 1 illustrates a perspective view of the balling gun of the present invention.

Referring to FIG. 1 there is shown a balling gun 1 constructed in accordance with the teachings of the present invention. A pair of finger grips 2 and 3 extend laterally to a barrel 8. These finger grips serve as the means for grasping and manipulating the balling gun 1. For reasons of strength, support webs 9 may extend intermediate each of finger grips 2 and 3 and barrel 8. A circular thumb grip 5 is attached to the extremity of a hollow shaft 4 extending from within barrel 8. Shaft 4 is slidable into and out of barrel 8 in response to movement of thumb grip 5 toward or away from finger grips 2 and 3, respectively.

The opposite end of barrel 8 is slit to form four resilient arms, as indicated by numeral 6. These arms are generally drawn toward one another in a contacting relationship with one another whereby they define a cross-sectional area approximately equivalent to the cross-sectional area of barrel 8. Arms 6 are, however, expandable from one another to receive a medicinal cartridge or bolus 7. The resilient nature of arms 6 causes the arms to exert a pressure upon the lateral surface of bolus 7 so as to prevent the bolus from sliding along its axis and also inhibit lateral movement of the bolus.

The internal constructional details of balling gun 1 will be described with particular reference to FIG. 2. The hollow shaft 4 is rigidly secured to thumb ring 5 and extends interior to barrel 8 within an annular recess 11. The axial movement of shaft 4 into barrel 8 is limited by shoulder 13 circumscribing shaft 4 and contacting extremity 18 of barrel 8. In the alternative, the end wall or shoulder 17 of recess 11 may be utilized to engage the extremity of shaft 4 and limit the axial movement of the shaft.

A plunger 10 extends interior to both shaft 4 and barrel 8. One end of plunger 10 is formed to include a flange 15 which flange seats within an annular cavity 16 formed as a part of thumb grip 5. To displace thumb grip 5 toward finger grips 2 and 3, it may be understood that the operator's thumb will be inserted within thumb grip 5 and adjacent flange 15 of plunger 10. Thus, displacement of thumb grip 5 will also cause shaft 4 and plunger 10 to be axially displaced within barrel 8 toward resilient arms 6. When thumb grip 5 is displaced away from finger grips 2 and 3, flange 15, engaging annular recess 16, will cause plunger 10 to be withdrawn from within barrel 8 by an amount equivalent to the withdrawal of shaft 4 from within the barrel.

As mentioned above, resilient arms 6 are laterally displaced to permit the insertion of a bolus 7 intermediate the arms. The lateral displacement of the arms is accomplished by a collar 14 mounted about plunger 10 in proximity to the inner surface 19 of the arms. The diameter of collar 14 is greater than the diameter of the passageway within barrel 8 housing plunger 10. Thus, when collar 14 is in engagement with a portion of the inner surfaces 19, that portion is inclined to the longitudinal axis of the barrel 8 as shown in the drawings. Thereby, as collar 14 is positionally displaced toward finger grips 2 and 3, it will cause the resilient arms 6 to be laterally displaced by a bending moment acting in proximity to the end of the slits defining the arms. The point at which the bending occurs is generally illustrated by numeral 20. As will be appreciated by those skilled in the art, the further collar 14 travels toward point 20, the greater will be the angular displacement of arms 6. In other words, the collar 14 is effective to radially expand the arms 6 with respect to each other in response to axial movement of plunger 10.

From the above discussion, it may therefore be appreciated that when thumb ring 5 is in its extended most position, collar 14 will be closest to point 20 and cause the maximum lateral expansion of resilient arms 6. The maximum lateral expansion of arms 6 is generally determinative of the maximum cross-sectional area bolus 7 that may be gripped by the balling gun 1 of the present invention.

As thumb grip 5 is forced toward finger grip 2 and 3, the plunger 10 will also be equivalently displaced causing collar 14 to be moved away from point 20. The further collar 14 moves, the less will be the lateral expansion of arms 6. At some point, the lateral expansion of arms 6 will be equivalent to the diameter or width of bolus 7, at which point collar 14 will become disengaged from the inner surfaces 19 of arms 6 and the resilient force of the arms will act directly upon the bolus to retain it. A continuing further movement of thumb ring 5 toward finger grips 2 and 3 will ultimately cause plunger 10 to come in contact with bolus 7. After the initial contact, further displacement of plunger 10 will eject bolus 7 from within arms 6.

Referring to FIG. 3, there is shown the structural details of arms 6. The ends of arms 6 are rounded and smooth to minimize or eliminate any scratching of the animal's mouth or throat by the arms themselves. The spacing intermediate each of the arms is tapered toward point 20 to permit the arms to come together in the absence of a bolus whereby they represent a cross-sectional area equal to or lesser than the cross-sectional area of barrel 8. The thickness of the arms may also be tapered from point 20 to prevent the collar 14 from impeding the closure of the arms. Hence, the discomfort to the animal is minimized to the greatest extent possible by minimizing the cross-sectional area of the inserted end of the balling gun. FIG. 3 also illustrates that bolus 7 may be an essentially rectangular cartridge with rounded corners as well as a generally cylindrically shaped bolus with domed ends as shown in FIGS. 1 and 2.

FIG. 4 illustrates a cross-sectional view of the end of balling gun 1, including a bolus 7, when the latter is inserted into an animal's throat. Not only are the ends of arms 6 curved as shown in FIG. 3, but the lateral edges of arms 6 are also curved to eliminate the possibility of any cutting action by the lateral sides. Further, FIG. 4 illustrates that arms 6 exert a pressure upon the horizontal and vertical sides of bolus 7 to prevent dislodgement of the bolus from in between the arms.

From the cross-sectional view shown in FIG. 4, it may also be appreciated that the total cross-sectional area of the apparatus inserted within an animal's throat has been minimized to that of the bolus itself plus the width and thickness of the four arms 6. As arms 6 are not circumferential about bolus 7 they tend to alleviate the strain imposed upon the animal's throat.

While the principles of the invention have now been made clear in an illustrative embodiment, there will be immediately obvious to those skilled in the art many modifications of structure, arrangement, proportions, the elements, materials, and components, used in the practice of the invention which are particularly adapted for specific environments and operating requirements without departing from those principles.

I claim:

1. A balling gun for administering a bolus within the throat of an animal, said balling gun comprising:
   a. an elongated barrel having a plurality of resilient arms disposed at one end thereof for grasping the bolus;
   b. said arms having inner surfaces which define a space within said gun to receive a bolus through an opening located at the end of the arms,
   c. a plunger extending through the other end of said barrel and slidably mounted for axial movement within said barrel with one end extending within the space defined by said arms;
   d. expansion means located within said space and secured to said plunger for engagement with a portion of said inner surfaces extending directly from said one end of the barrel with said portion being inclined with respect to the longitudinal axis and toward said other end of the barrel,
   e. said expansion means being effective to radially expand said arms in response to axial movement of said plunger toward said other end.

2. The apparatus as set forth in claim 1 wherein said resilient arms comprise at least three arms, said at least three arms being equiangularly disposed about the longtiudinal axis of said barrel.

3. The apparatus as set forth in claim 2 wherein said barrel is split into four arms.

4. The apparatus as set forth in claim 1 including finger grip means extending lateral to said barrel and a thumb grip connected to the other end of said plunger; whereby, said balling gun can be grasped and operated with one hand.

5. The apparatus as set forth in claim 4 wherein said thumb grip includes a hollow shaft slidably disposed within said other end of said barrel.

6. The apparatus as set forth in claim 5 wherein the ends of said arms are smoothly rounded to preclude injury to the animal's mouth and throat.

7. The apparatus as set forth in claim 6 wherein the longitudinal surface of each of said arms is smoothly rounded to preclude injury to the animal's mouth and throat.

8. The apparatus as set forth in claim 5 wherein said arms are tapered toward said one end of said barrel to permit said arms to contract and define a cross-sectional area less than the cross-sectional area of said barrel.

9. The apparatus as set forth in claim 1 wherein said expansion means comprises a collar secured about said plunger, said collar having a diameter greater than the inside diameter of the barrel.

10. The apparatus as set forth in claim 1 including means for effecting axial movement of said plunger.

* * * * *